United States Patent  
Ceci et al.

(10) Patent No.: US 7,026,475 B2  
(45) Date of Patent: Apr. 11, 2006

(54) POSITIVE ALLOSTERIC AMPA RECEPTOR MODULATORS (PAARM), PROCESSES FOR PREPARING THEM, AND THEIR USE AS PHARMACEUTICAL COMPOSITIONS

(75) Inventors: Angelo Ceci, Biberach (DE); Klaus Klinder, Oggelshausen (DE); Thomas Weiser, Nieder-Olm (DE); Karin Winter, Gau-Algesheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/699,374

(22) Filed: Oct. 31, 2003

(65) Prior Publication Data

US 2004/0116412 A1 Jun. 17, 2004

Related U.S. Application Data

(63) Continuation of application No. 10/141,208, filed on May 8, 2002, now abandoned.

(60) Provisional application No. 60/303,292, filed on Jul. 6, 2001.

(30) Foreign Application Priority Data

May 17, 2001 (DE) ................................ 101 23 952

(51) Int. Cl.  
    *C07D 279/02* (2006.01)  
    *A61K 31/5415* (2006.01)  
    *A61P 25/18* (2006.01)

(52) U.S. Cl. ......................................... 544/33; 544/14  
(58) Field of Classification Search .................. 544/33, 544/14  
See application file for complete search history.

(56) References Cited

U.S. PATENT DOCUMENTS 6,083,947 A 7/2000 Granger et al.  
2002/0013313 A1 1/2002 Winter et al.

FOREIGN PATENT DOCUMENTS

WO      WO 99/67242      12/1999  
WO      WO 9967242 A1 * 12/1999

OTHER PUBLICATIONS

R.R. Wilkening, et al., Synthesis and Activity of 2-(Sulfonamido)Methyl-Carbapenems: Discovery of a Novel, Anti-MRSA1,8-Naphthosultam Pharmacopore, Bioorganic & Medicinal Chemistry Letters 9, (1999) pp 673-678, Oxford, GB, Example 16: table 1.

* cited by examiner

*Primary Examiner*—James O. Wilson  
*Assistant Examiner*—Kahsay Habte  
(74) *Attorney, Agent, or Firm*—Michael P. Morris; Mary-Ellen M. Devlin; Alan Stempel

(57) ABSTRACT

Compounds of formula (I)

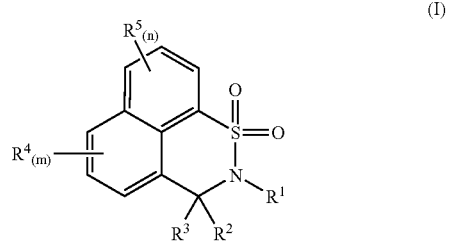

wherein $R^1$, $R^2$, $R^3$, $R^4$, $R^5$, n, and m, are as defined herein, or an enantiomer or diastereomer thereof, or a pharmacologically acceptable salt thereof, processes for preparing these compounds, and their use in pharmaceutical compositions.

7 Claims, No Drawings

POSITIVE ALLOSTERIC AMPA RECEPTOR MODULATORS (PAARM), PROCESSES FOR PREPARING THEM, AND THEIR USE AS PHARMACEUTICAL COMPOSITIONS

RELATED APPLICATIONS

This application is a continuation of U.S. application Ser. No. 10/141,208, filed May 8, 2002, now abandoned, which claims, as does the present application priority to U.S. provisional application Ser. No. 60/303,292, filed Jul. 6, 2001, the disclosures of all of which are incorporated by reference in their entirety.

BACKGROUND OF THE INVENTION

The present invention relates to new positive allosteric AMPA receptor modulators, processes for preparing them, and their use as pharmaceutical compositions.

Compounds which are structurally similar to the compounds according to the invention are disclosed in WO 99/67242 which describes carbapenem derivatives with an antibacterial activity, wherein naphtho[1,8-de]-2,3-dihydro-1,1-dioxide-1,2-thiazine is used as a synthesis component.

SUMMARY OF THE INVENTION

The compounds according to the invention are compounds of general formula (I)

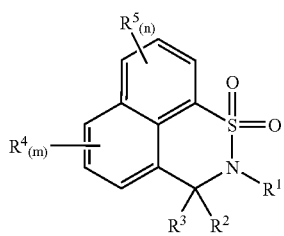

(I)

wherein:

R$^1$ denotes a group selected from among hydrogen, a C$_1$–C$_6$-alkyl group optionally substituted by one or more halogen atoms, —SO$_2$H, —SO$_2$—C$_1$–C$_6$-alkyl, —SO—C$_1$–C$_6$-alkyl, —CO—C$_1$–C$_6$-alkyl, —O, phenyl-C$_1$–C$_4$-alkyl, —C$_1$–C$_4$-alkyl-NR$^6$R$^7$, and —C$_1$–C$_4$-alkyl-O—C$_1$–C$_4$-alkyl, and C$_3$–C$_6$-cycloalkyl, R$^2$ and R$^3$, which may be identical or different, denote a group selected from among hydrogen, a C$_1$–C$_6$-alkyl group optionally substituted by one or more halogen atoms, halogen, —NO$_2$, —SO$_2$H, —SO$_2$—C$_1$–C$_6$-alkyl, —SO—C$_1$–C$_6$-alkyl, —CO—C$_1$–C$_6$-alkyl, —OH, —O—C$_1$–C$_6$-alkyl, —S—C$_1$–C$_6$-alkyl, —C$_1$–C$_4$-alkyl-NR$^6$R$^7$, and —C$_1$–C$_1$–$_4$-alkyl-O—C$_1$–C$_4$-alkyl, and C$_3$–C$_6$-cycloalkyl, or R$^1$ and R$^2$ together denote a C$_4$–C$_6$-alkylene bridge;

R$^6$ and R$^7$, which may be identical or different, denote hydrogen, C$_1$–C$_4$-alkyl, or —CO—C$_1$–C$_4$-alkyl;

R$^8$ and R$^9$, which may be identical or different, denote hydrogen or C$_1$–C$_4$-alkyl;

R$^4$, each of which may be identical or different, denotes a group selected from among a C$_1$–C$_6$-alkyl group optionally substituted by one or more halogen atoms, phenyl-C$_1$–C$_4$-alkyl, halogen, —CN, —NO$_2$, —SO$_2$H, —SO$_3$H, —SO$_2$—C$_1$–C$_6$-alkyl, —SO—C$_1$–C$_6$-alkyl, —SO$_2$—NR$^6$R$^7$, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, —NR$^6$R$^7$, and an aryl group optionally mono or polysubstituted by halogen atoms, —NO$_2$, —SO$_2$H, or C$_1$–C$_4$-alkyl;

R$^5$, each of which may be identical or different, denotes a group selected from among a C$_1$–C$_6$-alkyl group optionally substituted by one or more halogen atoms, phenyl-C$_1$–C$_4$-alkyl, halogen, —CN, —NO$_2$, —SO$_2$H, —SO$_3$H, —SO$_2$—C$_1$–C$_6$-alkyl, —SO—C$_1$–C$_6$-alkyl, —SO$_2$—NR$^6$R$^7$, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, —NR$^6$R$^7$, and an aryl group optionally mono or polysubstituted by halogen atoms, —NO$_2$, —SO$_2$H, or C$_1$–C$_4$-alkyl; and n and m, which may be identical or different, represent 0, 1, 2, or 3, with the proviso that naphtho[1,8-de]-2,3-dihydro-1,1-dioxide-1,2-thiazine is excluded, optionally in the form of their various enantiomers and diastereomers, and the pharmacologically acceptable salts thereof.

Preferred compounds are the compounds of general formula (I), wherein:

R$^1$ denotes a group selected from among hydrogen, a C$_1$–C$_6$-alkyl group optionally substituted by one or more halogen atoms, —SO$_2$H, —SO$_2$—C$_1$–C$_6$-alkyl, —SO—C$_1$–C$_6$-alkyl, —CO—C$_1$–C$_6$-alkyl, —O, —C$_1$–C$_4$-alkyl-NR$^7$R$^8$, and —C$_1$–C$_4$-alkyl-O—C$_1$–C$_4$, or benzyl, R$^2$ and R$^3$, which may be identical or different, denote a group selected from among hydrogen, a C$_1$–C$_6$-alkyl group optionally substituted by one or more halogen atoms, halogen, —NO$_2$, —SO$_2$H, —SO$_2$—C$_1$–C$_6$-alkyl, —SO—C$_1$–C$_6$-alkyl, —CO—C$_1$–C$_6$-alkyl, —OH, —O—C$_1$–C$_6$-alkyl, —S—C$_1$–C$_6$-alkyl, —C$_1$–C$_4$-alkyl-NR$^6$R$^7$, and —C$_1$–C$_4$-alkyl-O—C$_1$–C$_4$-alkyl, or R$^1$ and R$^2$ together denote a C$_4$–C$_6$-alkylene bridge;

R$^6$ and R$^7$, which may be identical or different, denote hydrogen, C$_1$–C$_4$-alkyl, or —CO—C$_1$–C$_2$-alkyl; and R$^4$, each of which may be identical or different, denotes a group selected from among a C$_1$–C$_6$-alkyl group optionally substituted by one or more halogen atoms, halogen, —CN, —NO$_2$, —SO$_2$H, —SO$_3$H, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, and —NR$^6$R$^7$;

R$^5$, each of which may be identical or different, denotes a group selected from among a C$_1$–C$_6$-alkyl group optionally substituted by one or more halogen atoms, halogen, —CN, —NO$_2$, —SO$_2$H, —SO$_3$H, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, and —NR$^6$R$^7$; and n and m, which may be identical or different, represent 0, 1, or 2, optionally in the form of the various enantiomers and diastereomers thereof, as well as the pharmacologically acceptable salts thereof.

Particularly preferred are compounds of general formula (I), wherein:
$R^1$ denotes hydrogen, $C_1$–$C_4$-alkyl, or benzyl,
$R^2$ and $R^3$, which may be identical or different, denote hydrogen or $C_1$–$C_4$-alkyl, or
$R^1$ and $R^2$ together denote a butylene bridge;
$R^4$, each of which may be identical or different, denotes a group selected from among a $C_1$–$C_6$-alkyl group optionally substituted by one or more halogen atoms, halogen, —CN, —NO$_2$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—NR$^6$R$^7$, —OH, —O—$C_1$–$C_6$-alkyl, —S—$C_1$–$C_6$-alkyl, and —NR$^6$R$^7$;
$R^5$, each of which may be identical or different, denotes a group selected from among a $C_1$–$C_6$-alkyl group optionally substituted by one or more halogen atoms, halogen, —CN, —NO$_2$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—NR$^6$R$^7$, —OH, —O—$C_1$–$C_6$-alkyl, —S—$C_1$–$C_6$-alkyl, and —NR$^6$R$^7$; and
n and m, which may be identical or different, represent 0, 1, or 2,
optionally in the form of the various enantiomers and diastereomers thereof, as well as the pharmacologically acceptable salts thereof.

Also particularly preferred are compounds of general formula (I), wherein:
$R^1$, $R^2$, and $R^3$, which may be identical or different, denote hydrogen or $C_1$–$C_4$-alkyl;
$R^4$, which may be identical or different, denotes a group selected from among a $C_1$–$C_6$-alkyl group optionally substituted by one or more halogen atoms, halogen, —NO$_2$, —O—CO—$C_1$–$C_4$-alkyl, —O—CO—O—$C_1$–$C_4$-alkyl, —O—$C_1$–$C_6$-alkyl, and —NR$^6$R$^7$;
$R^5$, which may be identical or different, denotes a group selected from among a $C_1$–$C_6$-alkyl group optionally substituted by one or more halogen atoms, halogen, —NO$_2$, —O—CO—$C_1$–$C_4$-alkyl, —O—CO—O—$C_1$–$C_4$-alkyl, —O—$C_1$–$C_6$-alkyl, and —NR$^6$R$^7$; and
n and m, which may be identical or different, represent 0, 1, or 2,
optionally in the form of the various enantiomers and diastereomers thereof, as well as the pharmacologically acceptable salts thereof.

Of particular importance according to the invention are the compounds of general formula (I), wherein $R^1$ denotes methyl, ethyl, isopropyl, n-butyl, or benzyl, optionally in the form of the various enantiomers and diastereomers thereof, as well as the pharmacologically acceptable salts thereof.

Particularly preferred are compounds of general formula (I) wherein $R^1$ denotes methyl, optionally in the form of the pharmacologically acceptable salts thereof.

Also particularly preferred are compounds of general formula (I), wherein:
$R^1$ denotes methyl;
$R^2$ and $R^3$ denote hydrogen;
$R^4$ and $R^5$, which may be identical or different, denote halogen, preferably fluorine, chlorine, or bromine, most preferably fluorine or chlorine; and
n and m, which may be identical or different, represent 0, 1, or 2, preferably 0 or 1,
optionally in the form of the pharmacologically acceptable salts thereof.

The alkyl groups used, unless otherwise stated, are branched and unbranched alkyl groups having 1 to 6 carbon atoms, preferably 1 to 4 carbon atoms. Examples include: methyl, ethyl, propyl, butyl, pentyl, and hexyl. The groups methyl, ethyl, propyl, or butyl may optionally also be referred to by the abbreviations Me, Et, Pr, or Bu. Unless otherwise stated, the definitions propyl, butyl, pentyl, and hexyl also include all possible isomeric forms of the groups in question. Thus, for example, propyl includes n-propyl and isopropyl, butyl includes isobutyl, sec-butyl, and tert-butyl, etc.

In the above mentioned alkyl groups, one or more hydrogen atoms may optionally be substituted by the halogen atoms fluorine, chlorine, bromine, or iodine. The substituents fluorine and chlorine are preferred. The substituent fluorine is particularly preferred. If desired, all the hydrogen atoms of the alkyl group may be replaced.

The alkyl group mentioned in the group phenyl-$C_1$–$C_4$-alkyl may be in branched or unbranched form. Unless otherwise stated benzyl and phenylethyl are preferred phenyl-$C_1$–$C_4$-alkyl groups. Benzyl is particularly preferred.

The alkyl groups mentioned in the groups —SO$_2$—$C_1$–$C_6$-alkyl, —SO—$C_1$–$C_6$-alkyl, —CO—$C_{1-C6}$-alkyl, —CO—$C_1$–$C_4$-alkyl, —$C_1$–$C_4$-alkyl-NR$^6$R$^7$, —$C_1$–$C_4$-alkyl-O—$C_1$–$C_6$-alkyl, —O—$C_1$–$C_6$-alkyl, —S—$C_1$–$C_6$-alkyl, —O—CO—$C_1$–$C_4$-alkyl, —CO—O—$C_1$–$C_4$-alkyl, or —O—CO—O—$C_1$–$C_4$-alkyl may be in branched or unbranched form with 1 to 6 carbon atoms, preferably with 1 to 4 carbon atoms, particularly preferably with 1 to 3 carbon atoms, most preferably with 1 to 2 carbon atoms.

The $C_4$–$C_6$-alkylene bridge may, unless otherwise stated, be branched and unbranched alkylene groups having 4 to 6 carbon atoms, for example, n-butylene, 1-methylpropylene, 2-methylpropylene, 1,1-dimethylethylene, 1,2-dimethylethylene, etc. n-Butylene bridges are particularly preferred.

The aryl group is an aromatic ring system having 6 to 10 carbon atoms, preferably phenyl.

In the above mentioned aryl groups, one or more hydrogen atoms may optionally be substituted by halogen atoms, —NO$_2$, —SO$_2$H, or —$C_1$–$C_4$-alkyl, preferably fluorine, chlorine, —NO$_2$, ethyl, or methyl, most preferably fluorine or methyl.

The term $C_3$–$C_6$-cycloalkyl denotes saturated cyclic hydrocarbon groups having 3 to 6 carbon atoms, for example, cyclopropyl, cyclobutyl, cyclopentyl, or cyclohexyl.

The term halogen, unless otherwise stated, refers to fluorine, chlorine, bromine, and iodine, preferably fluorine, chlorine, and bromine, most preferably fluorine and chlorine, most preferably fluorine.

As already mentioned, the compounds of formula (I) or the various enantiomers and diastereomers thereof may be converted into the salts thereof, particularly, for pharmaceutical use, into the physiologically and pharmacologically acceptable salts thereof. These salts may on the one hand take the form of physiologically and pharmacologically acceptable acid addition salts of the compounds of formula (I) with inorganic or organic acids. On the other hand, the compound of formula (I) where $R^1$ is hydrogen may be converted by reaction with inorganic bases into physiologically and pharmacologically acceptable salts with alkali or alkaline earth metal cations as counter-ions. The acid addition salts may be prepared, for example, using hydrochloric acid, hydrobromic acid, sulfuric acid, phosphoric acid, methanesulfonic acid, acetic acid, fumaric acid, succinic acid, lactic acid, citric acid, tartaric acid, or maleic acid. It is also possible to use mixtures of the above acids. For preparing the alkali and alkaline earth metal salts of the compound of formula (I) wherein $R^1$ denotes hydrogen, it is preferable to use the alkali and alkaline earth metal hydroxides and hydrides, the hydroxides and hydrides of the alkali metals, especially sodium and potassium, being preferred, while sodium and potassium hydroxide are particularly preferred.

DETAILED DESCRIPTION OF THE INVENTION

The compounds according to the invention may be prepared in a manner known per se. The following general methods of synthesis 1 and 2 shown in Diagrams 1 and 2 below are meant to illustrate the invention without restricting it to their content.

Method 1

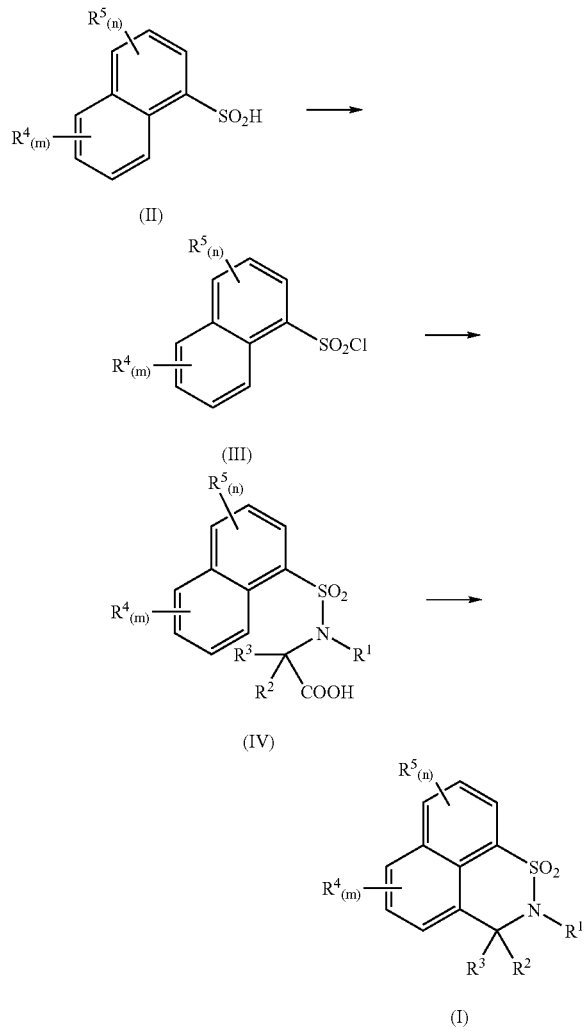

Starting from a compound of formula (II), a compound of formula (III) is prepared by sulfonation and subsequent chlorination. The compound of formula (IV) obtained after condensation with aminoacetic acid derivatives is cyclized by adding polyphosphoric acid to the target compound (I).

The general preparation of the compounds according to the invention in accordance with Diagram 1 is described in detail hereinafter.

Sulfonation of the Naphthalene Derivative (II)

About 10 mmol of the naphthalene derivative (II) are taken up in 2 mL to 100 mL, preferably 3 mL to 80 mL, most preferably about 4 mL, of acetic anhydride and 10 mmol to 100 mmol, preferably 11 mmol to 80 mmol, particularly preferably 11 mmol or concentrated sulfuric acid is added at 0° C. to 50° C., preferably 5° C. to 20° C., particularly preferably about 18° C. After 2 hours to 16 hours, preferably about 5 hours, stirring at 20° C. to 100° C., preferably about 25° C., the mixture is poured onto a saturated NaCl solution. The crystals formed are isolated.

Methylene chloride, diisopropylether, ethyl acetate, trichloromethane, toluene, benzene, or 1,4-dioxane may be used instead of acetic acid anhydride, while fuming sulfuric acid, sulfur trioxide, chlorine sulfates or combinations thereof may be used as an alternative to concentrated sulfuric acid.

Synthesis of the Naphthalene-1-sulfonic Acid Chlorides (III)

About 10 mmol of the naphthalene-1-sulfonic acids are combined successively with 10 mmol to 500 mmol, preferably about 90 mmol, of phosphorus oxytrichloride and 8 mmol to 50 mmol, preferably about 10 mmol, of phosphorus pentachloride and heated for 2 hours to 16 hours, preferably about 5 hours, at 20° C. to 100° C., preferably by refluxing. Then the reaction mixture is evaporated down and combined with water. After extraction with organic diluent, the combined organic extracts are dried and freed from solvent. The crude product obtained is used in the subsequent steps without being purified.

Instead of the phosphorus oxytrichloride/phosphorus pentachloride mixture, thionyl chloride, phosphorus pentachloride, a phosphoric acid/chlorine mixture, or phosgene may be used. The reaction may alternatively be carried out in the diluents ethyl acetate, water, acetonitrile, N,N-dimethylacetamide, sulfolane, DMF, hexane, or dichloroethane.

Synthesis of the Naphthalene-1-sulfonylaminoacetic Acids

About 10 mmol of the chlorosulfonylnaphthalenes, 10 mmol to 100 mmol, preferably 11 mmol to 30 mmol, most preferably about 12 mmol, of aminoacetic acid and 10 mmol to 100 mmol, preferably 11 mmol to 30 mmol, most preferably about 12 mmol, of sodium hydroxide are dissolved in water and toluene. The reaction mixture is stirred for 2 hours to 16 hours at 0° C. to 110° C., preferably at about 65° C., then the phases are separated. The aqueous phase is acidified and extracted. The combined organic extracts are dried and evaporated down. Purification may be carried out by chromatography.

Triethylamine, potassium carbonate, sodium hydrogen carbonate, or sodium hydride may be used instead of sodium hydroxide, while tetrahydrofuran, diethylether, dichloromethane, trichloromethane, dioxane, acetone, benzene, ethanol, methanol, ethyl acetate, or acetonitrile may be used instead of toluene.

Cyclization of the Naphthalene-1-sulfonylaminoacetic Acids (IV)

About 10 mmol of the naphthalene-1-sulfonylaminoacetic acids are combined with 10 g to 200 g, preferably about 40 g, of polyphosphoric acid and stirred for 2 hours to 16 hours, preferably about 5 hours, at 20° C. to 110° C., preferably 75° C. to 95° C., most preferably at about 80° C. Then the reaction mixture is poured onto water and extracted. The combined organic extracts are dried and evaporated down. The residue is purified.

Method 2

Diagram 2

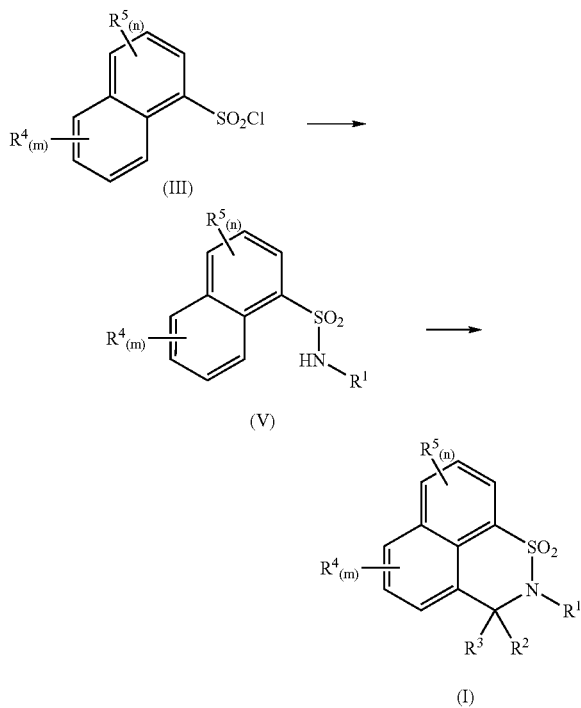

The compounds of formula (III) obtained as intermediate compounds in Method 1 are reacted with primary amines to obtain the compounds of formula (V) and then cyclized by the addition of a compound of formula $R^2R^3C=O$ in the presence of strong acid to obtain the target compounds (I).

In order to prepare the compounds of formula (I) wherein $R^1$ and $R^2$ represent hydrogen, paraformaldehyde, trioxane, or formalin may be used and methanesulfonic acid, trifluoroacetic acid, sulfuric acid, phosphoric acid, or polyphosphoric acid may be used as strong acids.

The general preparation of the compounds according to the invention in accordance with Diagram 2 is described in detail hereinafter.

Synthesis of the Naphthalenesulfonamides (V)

About 10 mmol of the chlorosulfonylnaphthalenes (III) are combined with an alcoholic solution of the primary amine (10 mmol to 1000 mmol in 5 mL to 200 mL, for example, 200 mmol in 50 mL ethanol) and then heated to 0° C. to 100° C. for 2 hours to 16 hours, preferably about 5 hours, preferably by refluxing. Then the reaction mixture is evaporated down and purified.

Instead of the alcoholic solvent, it is also possible to use toluene, benzene, trichloromethane, dichloromethane, diethylether, tetrahydrofuran, water, acetonitrile, acetic anhydride, acetone, pyridine, dimethylsulfoxide, dimethylformamide, dioxane, or hexane.

Cyclization of the Naphthalene-1-sulfonamides (V) to Form the Target Compounds (I)

About 10 mmol of the naphthalene-1-sulfonamides are added to 0 mL to 100 mL, preferably 20 mL to 80 mL, most preferably about 40 mL of methanesulfonic acid and combined with a solution of 3 mmol to 50 mmol, preferably 4 mmol to 30 mmol, most preferably 5 mmol of trioxane in 0 mL to 100 mL, preferably about 12 mL, of trifluoroacetic acid. The reaction mixture is stirred for 2 hours to 16 hours, preferably 5 hours, at 20° C. to 100° C., preferably 30° C. to 80° C., most preferably about 35° C. and then poured onto ice water. After extraction and drying of the combined organic extracts, the solution is evaporated down. The crude product is purified.

Instead of trioxane, it is possible to use paraformaldehyde or formalin, while instead of trifluoroacetic acid it is possible to use boron trifluoride-diethylether, acetic acid, polyphosphoric acid, phosphoric acid, or sulfuric acid. Acetic anhydride or dichloromethane may be used as possible diluents.

The new compounds of general formula (I) may be synthesized analogously to the following Examples of synthesis. These Examples are, however, intended solely as examples of procedure to illustrate the invention further without restricting it to the subject matter thereof.

EXAMPLE 1

Synthesis of 2-methyl-2,3-dihydronaphtho[1,8-de][1,3]thiazine-1,1-dioxide 2.21 g of N-methyl-1-naphthalenesulfonic acid amide is dissolved in 25 mL of methanesulfonic acid at 35° C. and combined with a solution of 0.30 g of trioxane in 8 mL of trifluoroacetic acid. After 2 hours stirring at ambient temperature, the reaction mixture is poured onto 300 mL of ice water. The solid formed is separated off by filtration, washed with 100 mL of water, and dried overnight. After crystallization from methylcyclohexane, the product is isolated as a white solid. Yield: 2.20 g; m.p.: 136° C.

EXAMPLE 2

Synthesis of 6-chloro-2-methyl-2,3-dihydronaphtho[1,8-de][1,3]thiazine-1,1-dioxide 0.45 g of 5-chloro-naphthalene-1-sulfonic acid-N-methylamide is dissolved in 6.8 mL of methanesulfonic acid at 35° C. and combined with a solution of 0.07 g of trioxane in 2 mL of trifluoroacetic acid. After 2 hours stirring at 35° C., the reaction mixture is poured onto 100 mL of ice water and the aqueous phase is extracted with ethyl acetate. The organic extracts collected are dried with sodium sulfate, evaporated down in vacuo, and then purified by chromatography. Yield: 0.41 g; m.p.: 150° C.

EXAMPLE 3

Synthesis of 2,3-dihydronaphtho[1,8-de][1,3]thiazine-1,1-dioxide

Naphthalene-1-sulfonic acid tert-butylamide 8 mL of tert-butylamine is placed in 50 mL of chloroform, cooled to 0° C., and 5.75 g of 1-naphthalenic acid chloride in 45 mL of chloroform are added dropwise. Then the mixture is stirred for 24 hours at ambient temperature. After concentration by evaporation in vacuo, the residue obtained is dissolved in dichloromethane and washed with 2 N hydrochloric acid. The organic extracts collected are dried with sodium sulfate and evaporated down in vacuo. Yield: 5.48 g.

2-tert-butyl-1,1-dioxo-1,2-dihydro-1λ$^6$-naphtho[1,8-de][1,3]thiazin-3-one 4.36 g of naphthalene-1-sulfonic acid tert-butylamide is placed in 80 mL tetrahydrofuran, cooled to −10° C., and 29 mL of N-butyl lithium (1.6 molar solution in hexane) are cautiously added dropwise. The mixture is first stirred for 0.5 hour at −10° C., then for 3 hours at ambient temperature. Then it is cooled to −5° C. and within 0.25 hour, $CO_2$ obtained from dry ice is piped in. The reaction mixture is stirred for 2.5 hours at ambient temperature, then combined with water. The solution is poured onto 4 N hydrochloric acid and extracted with ethyl acetate. The organic extracts collected are dried with sodium sulfate and, after evaporation in vacuo, purified by chromatography. Yield: 0.42 g.

2-tert-butyl-2,3-dihydronaphtho[1,8-de][1,3]thiazine-1,1-dioxide 0.17 g of 2-tert-butyl-1,1-dioxo-1,2-dihydro-1λ$^6$-naphtho[1,8-de][1,3]thiazin-3-one is suspended in 2 mL tetrahydrofuran at ambient temperature and 1.17 mL of borane-tetrahydrofuran complex (1 molar solution) is added. Then the mixture is refluxed with stirring for 100 hours, with a total of a further 8.2 mL of 1M borane-tetrahydrofuran complex solution being added in several batches. The reaction mixture is combined with 2 mL of 2 N hydrochloric acid and with 2 mL of methanol, then refluxed for 12 hours with stirring. 2 mL of ammonia is added and any crystals formed are filtered off. The filtrate is extracted with ethyl acetate and the organic extracts collected are dried with sodium sulfate. After evaporation in vacuo, the residue obtained is purified by chromatography. Yield: 0.06 g.

2,3-Dihydronaphtho[1,8-de][1,3]thiazine-1,1-dioxide 0.06 g of 2-tert-butyl-2,3-dihydro-naphtho[1,8-de][1,3]thiazin-1,1-dioxide is dissolved in 1 mL of dichloromethane and 0.02 mL of trifluoroacetic acid is added. Then the mixture is stirred for a total of 22 hours at reflux temperature and for 96 hours at ambient temperature, while during this period a total of 0.07 mL of trifluoroacetic acid is added. The reaction mixture is evaporated down in vacuo and purified by chromatography. Yield: 0.034 g; m.p.: 206° C.–207° C.

EXAMPLE 4

Synthesis of [2-(1,1-dioxo-1H-3H-1λ$^6$-naphtho[1,8-de]thiazine-2-yl)ethyl]dimethylamine 0.028 g of sodium hydride is suspended in 0.5 mL of dimethylformamide and 0.073 g of 2,3-dihydro-naphtho[1,8-de][1,3]thiazin-1,1-dioxide in 1 mL of dimethylformamide is added. Then 0.053 g of diethylaminoethyl chloride-hydrochloride are added batchwise. The reaction mixture is stirred for 18 hours at ambient temperature and then poured onto ice water. The mixture is extracted with dichloromethane and the organic extracts collected are dried with sodium sulfate. After evaporation in vacuo, the residue obtained is purified by chromatography. Yield: 0.035 g; m.p.: 97° C.–98° C.

EXAMPLE 5

Synthesis of N-(2-methyl-1,1-dioxo-2,3-dihydro-1H-1λ$^6$-naphtho[1,8-de][1,3]thiazin-6-yl)-acetamide 5-acetylaminonaphthalene-1-sulfonylchloride 1.40 g of 5-acetylaminonaphthalene-1-sulfonic acid and 2.23 g of phosphorus pentachloride are combined and stirred for 4 hours at 60° C. Then the solution is poured onto ice water and extracted with dichloromethane. The organic extracts collected are dried with sodium sulfate and evaporated down in vacuo. Yield: 1.10 g.

N-(5-methylsulfamoylnaphthalene-1-yl)-acetamide 1.10 g of 5-acetylaminonaphthalene-1-sulfonyl chloride is dissolved in 8 mL of ethanol and 8 mL of methylamine solution in ethanol are added dropwise. Then the resulting mixture is stirred at reflux temperature for 3.5 hours and the solvent is distilled off in vacuo. The residue is purified by chromatography. Yield: 0.50 g.

N-(2-methyl-1,1-dioxo-2,3-dihydro-1H-1λ$^6$-naphtho[1,8-de][1,3]thiazin-6-yl)-acetamide 0.25 g of N-(5-methylsulfamoylnaphthalene-1-yl)-acetamide is dissolved in 3.4 mL of methanesulfonic acid at 35° C. and combined with a solution of 0.027 g of trioxane in 1 mL of trifluoroacetic acid. After 6 hours stirring at 35° C., the reaction mixture is poured onto ice water and the aqueous phase extracted with ethyl acetate. The organic extracts collected are dried with sodium sulfate, evaporated down in vacuo, and purified by chromatography. Yield: 0.136 g; m.p.: 189° C.–190° C.

EXAMPLE 6

Synthesis of 2-(1,1-Dioxo-1H,3H-1λ$^6$-naphtho[1,8-de][1,3]thiazin-2-yl)-acetamide 8-tert-butylsulfamoylnaphthalene-1-carboxylic acid 4.36 g of naphthalene-1-sulfonic acid tert-butylamide are placed in 80 mL tetrahydrofuran, cooled to −10° C., and 29 mL of N-butyl lithium (1.6 molar solution in hexane) are cautiously added dropwise. The mixture is stirred first for 0.5 hour at −10° C., then for 3 hours at ambient temperature. It is then cooled to −5° C. and $CO_2$ obtained from dry ice is piped in within 0.25 hour. The reaction mixture is stirred for 2.5 hours at ambient temperature and then combined with water. The solution is poured onto 4 N hydrochloric acid and extracted with ethyl acetate. The organic extracts collected are dried with sodium sulfate and, after evaporation in vacuo, purified by chromatography. Yield: 1.19 g.

1,1-Dioxo-1,1-dihydro-1λ$^6$-naphtho[1,8-de][1,3]thiazin-3-one 0.25 g of polyphosphoric acid and 0.15 g of 8-tert-butylsulfamoylnaphthalene-1-carboxylic acid are combined. The mixture is stirred for 4 hours at 150° C. Then the reaction mixture is poured onto ice water and the aqueous phase is extracted with ethyl acetate. The organic extracts collected are dried with sodium sulfate and evaporated down in vacuo. Yield: 0.07 g.

2,3-Dihydronaphtho[1,8-de][1,3]thiazine-1,1-dioxide 0.07 g of 1,1-dioxo-1,1-dihydro-1$\lambda^6$-naphtho[1,8-de][1,3]thiazin-3-one is dissolved in 2 mL of tetrahydrofuran and then 1.2 mL of 1 molar borane-tetrahydrofuran complex solution is carefully added dropwise. The mixture is stirred for 18 hours at reflux temperature. The reaction mixture is combined with 1.5 mL of 2 N hydrochloric acid and 2 mL of methanol, then stirred for 2 hours at reflux temperature. 2 mL of ammonia is added and any crystals formed are filtered off. The filtrate is extracted with ethyl acetate, the organic extracts collected are dried with sodium sulfate and evaporated down in vacuo. Yield: 0.06 g.

2-(1,1-Dioxo-1H,3H-1$\lambda^6$-naphtho[1,8-de][1,3]thiazin-2-yl)-acetamide 0.011 g of sodium hydride is suspended in 0.5 mL of dimethylformamide, and 0.06 g of 2,3-dihydronaphtho[1,8-de][1,3]thiazine-1,1-dioxide in 1 mL of dimethylformamide is added. The mixture is stirred for 1 hour at ambient temperature and then 0.042 g of 2-bromoacetamide are added batchwise. Then the mixture is stirred for 18 hours at ambient temperature. The reaction mixture is poured onto ice water and extracted with dichloromethane. The organic extracts collected are dried with sodium sulfate and, after evaporation in vacuo, purified by chromatography. Yield: 0.043 g; m.p.: 195° C.–196° C.

EXAMPLE 7

Synthesis of 7-hydroxy-2-methyl-2,3-dihydronaphtho[1,8-de][1,3]thiazine-1,1-dioxide 0.6 g of 7-methoxy-2-methyl-2,3-dihydronaphtho[1,8-de][1,3]thiazine-1,1-dioxide is dissolved in 23 mL dichloromethane and the solution is cooled to −78° C. 2.3 mL of boron tribromide (1 molar solution in dichloromethane) is added dropwise. Then the mixture is stirred for 24 hours at ambient temperature. After evaporation in vacuo, the residue is purified by chromatography. Yield: 0.36 g; m.p.: 245° C.–246° C.

EXAMPLE 8

Synthesis of methyl 2-methyl-1,1-dioxo-2,3-dihydro-1H-1,6-naphtho[1,8-de][1,3]thiazin-7-yl ester carboxylate 0.11 g of 7-hydroxy-2-methyl-2,3-dihydronaphtho[1,8-de][1,3]thiazine-1,1-dioxide and 0.061 mL triethylamine are placed in 2 mL toluene and cooled to 0° C. 0.037 mL of methyl chloroformate are added dropwise. Then the mixture is stirred for 5 hours at ambient temperature. The suspension is then poured onto ice water and extracted with ethyl acetate. The organic extracts collected are dried with sodium sulfate and, after evaporation in vacuo, purified by chromatography. Yield: 0.065 g; m.p.: 161° C.–162° C.

The following compounds of formula (IA) are obtained, inter alia, analogously to the procedure described hereinbefore:

TABLE 1

(IA)

| Example | $R^1$ | $R^2$ | $R^3$ | $R^4$ | $R^5$ | $R^6$ | m.p. (° C.) |
|---|---|---|---|---|---|---|---|
| 9 | $CH_3$ | H | H | H | H | Br | 226–227 |
| 10 | $CH_3$ | $NO_2$ | H | H | H | H | 264–265 |
| 11 | $CH_3$ | H | H | $OCH_3$ | H | H | 174–175 |
| 12 | $CH_3$ | H | H | F | H | H | 129–130 |
| 13 | $CH_3$ | H | H | Br | H | H | 163–164 |
| 14 | $CH_3$ | H | H | $CH_3$ | H | H | 142–143 |
| 15 | $CH_3$ | H | H | I | H | H | 192–193 |
| 16 | $CH_3$ | I | H | H | H | H | 160–161 |
| 17 | $CH_3$ | H | $NO_2$ | H | H | H | 169–170 |
| 18 | $CH_3$ | H | OH | H | H | H | 160–161 |
| 19 | $CH_3$ | $N(CH_3)_2$ | H | H | H | H | |
| 20 | $CH_3$ | H | H | H | H | $N(CH_3)_2$ | |
| 21 | $CH_3$ | i-Pr | H | H | i-Pr | H | |
| 22 | $CH_3$ | H | OCOMe | H | H | H | |
| 23 | $CH_3$ | H | F | H | H | H | |

It has been found that the compounds of general formula (1) are characterized by their wide range of applications in the therapeutic field. Particular mention should be made of those applications in which the positive modulation of AMPA receptors plays a part.

The effect of the compounds according to the invention as AMPA receptor modulators was measured electrophysiologically on cells which express functional AMPA receptors. Investigations were carried out to see whether the test substances have a positive allosteric influence on the agonist-induced current.

The test was carried out at concentrations of between 0.3 μmol and 300 μmol.

TABLE 2

Intensification of the Agonist-Induced Current

| Example | Activity |
|---------|----------|
| 1 | + |
| 2 | + + |

Legend: + good; + + very good

The new compounds can also be used to treat illnesses or conditions in which neuronal networks which require AMPA receptors in order to function are damaged or limited in their function.

The compounds of general formula (I) can thus be used in dementias, in neurodegenerative or psychotic illnesses and in neurodegenerative disorders and cerebral ischemias of various origins, preferably in schizophrenia or learning and memory disorders.

The following are also included: epilepsy, hypoglycemia, hypoxia, anoxia, cerebral trauma, brain edema, amyotrophic lateral sclerosis, Huntington's Disease, Alzheimer's disease, sexual dysfunction, disorders of sensory/motor function, memory formation, hyperkinetic behavioral changes (particularly in children), hypotension, cardiac infarct, cerebral pressure (increased intracranial pressure), ischemic and hemorrhagic stroke, global cerebral ischaemia on stoppage of the heart, acute and chronic neuropathic pain, diabetic polyneuropathy, tinnitus, perinatal asphyxia, psychosis, Parkinson's disease and depression, and related anxiety states.

The new compounds may also be given in conjunction with other active substances, such as those used for the same indications or, for example, with neuroleptics, nootropics, psychostimulants, etc. They may be administered topically, orally, transdermally, nasally, parenterally, or by inhalation. Moreover, the compounds of general formula (I) or the salts thereof may also be combined with active substances of other kinds.

The compounds of general formula (I) may be given on their own or in conjunction with other active substances according to the invention, and possibly also in conjunction with other pharmacologically active substances. Suitable preparations include, for example, tablets, capsules, suppositories, solutions (particularly solutions for injection (s.c., i.v., and i.m.) and infusion), elixirs, emulsions, or dispersible powders. The content of the pharmaceutically active compound(s) should be in the range from 0.1 wt. % to 90 wt. %, preferably 0.5 wt. % to 50 wt. % of the composition as a whole, i.e., in amounts which are sufficient to achieve the dosage range specified below.

Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g., with the addition of isotonic agents, preservatives such as p-hydroxybenzoates, or stabilizers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as e.g., natural mineral powders (e.g., kaolins, clays, talc, chalk), synthetic mineral powders (e.g., highly dispersed silicic acid and silicates), sugars (e.g., cane sugar, lactose, and glucose) emulsifiers (e.g., lignin, spent sulfate liquors, methylcellulose, starch, and polyvinylpyrrolidone) and lubricants (e.g., magnesium stearate, talc, stearic acid, and sodium lauryl sulfate).

The preparations are administered by the usual methods, preferably by oral or transdermal route, particularly orally. For oral administration, the tablets may of course contain, apart from the above mentioned carriers, additives such as sodium citrate, calcium carbonate, and dicalcium phosphate together with various additives such as starch, preferably potato starch, gelatine, and the like. Moreover, lubricants such as magnesium stearate, sodium lauryl sulfate, and talc may be used at the same time for the tabletting process. In the case of aqueous suspensions, the active substances may be combined with various flavor enhancers or colorings in addition to the excipients mentioned above.

For parenteral use, solutions of the active substances with suitable liquid carriers may be used.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation, and the time or interval over which the drug is administered. Thus, in some cases, it may be sufficient to use less than the minimum dose given above, whereas in other cases, the upper limit may have to be exceeded. When administering large amounts, it may be advisable to divide them up into a number of smaller doses spread over the day.

The following examples of formulations illustrate the present invention without restricting its scope:

Examples of Pharmaceutical Formulations

| Tablets | per Tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely-ground active substance, lactose and some of the maize starch are mixed together. The mixture is screened, then moistened with a solution of polyvinylpyrrolidone in water, kneaded, wet-granulated and dried. The granules, the remaining maize starch and the magnesium stearate are screened and mixed together. The mixture is compressed to produce tablets of suitable shape and size.

| Tablets | per Tablet |
|---|---|
| active substance | 80 mg |
| lactose | 55 mg |
| maize starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| Ampoule Solution | |
|---|---|
| active substance | 50 mg |
| sodium chloride | 50 mg |
| aqua for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

We claim:

1. A compound of formula (I)

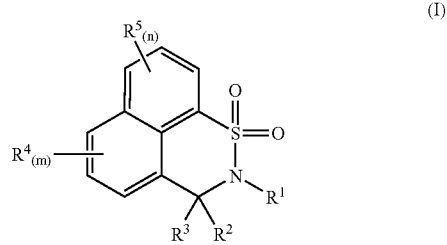

wherein:

R$^1$ is selected from hydrogen, a C$_1$–C$_6$-alkyl group optionally substituted by one or more halogen atoms, —SO$_2$H, —SO$_2$—C$_1$–C$_6$-alkyl, —SO—C$_1$–C$_6$-alkyl, —CO—C$_1$–C$_6$-alkyl, phenyl-C$_1$–C$_4$-alkyl, —C$_1$–C$_4$-alkyl-NR$^6$R$^7$, —C$_1$–C$_4$-alkyl-O—C$_1$–C$_4$-alkyl, or C$_3$–C$_6$-cycloalkyl, R$^2$ and R$^3$, which are identical or different, are each selected from hydrogen, a C$_1$–C$_6$-alkyl group optionally substituted by one or more halogen atoms, halogen, —NO$_2$, —SO$_2$H, —SO$_2$—C$_1$–C$_6$-alkyl, —SO—C$_1$–C$_6$-alkyl, —CO—C$_1$–C$_6$-alkyl, —OH, —O—C$_1$–C$_6$-alkyl, —S—C$_1$–C$_6$-alkyl, —C$_1$–C$_4$-alkyl-NR$^6$R$^7$, and —C$_1$–C$_4$-alkyl-O—C$_1$–C$_4$-alkyl, C$_3$–C$_6$-cycloalkyl, or R$^1$ and R$^2$ together are a C$_4$–C$_6$-alkylene bridge;

R$^6$ and R$^7$, which are identical or different, are each hydrogen, C$_1$–C$_4$-alkyl, or —CO—C$_1$–C$_4$-alkyl;

R$^4$, each of which are identical or different, are each selected from a C$_1$–C$_6$-alkyl group optionally substituted by one or more halogen atoms, phenyl-C$_1$–C$_4$-alkyl, halogen, —CN, —NO$_2$, —SO$_2$H, —SO$_3$H, —SO$_2$—C$_1$–C$_6$-alkyl, —SO—C$_1$–C$_6$-alkyl, —SO$_2$—NR$^6$R$^7$, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, —N$^6$R$^7$, an aryl group optionally mono or polysubstituted by halogen atoms, —NO$_2$, —SO$_2$H, or C$_1$–C$_4$-alkyl;

R$^5$, each of which are identical or different, are each selected from a C$_1$–C$_6$-alkyl group optionally substituted by one or more halogen atoms, phenyl-C$_1$–C$_4$-alkyl, halogen, —CN, —NO$_2$, —SO$_2$H, —SO$_3$H, —SO$_2$—C$_1$–C$_6$-alkyl, —SO—C$_1$–C$_6$-alkyl, —SO$_2$—NR$^6$R$^7$, —COOH, —CO—C$_1$–C$_6$-alkyl, —O—CO—C$_1$–C$_4$-alkyl, —CO—O—C$_1$–C$_4$-alkyl, —O—CO—O—C$_1$–C$_4$-alkyl, —CO—NR$^6$R$^7$, —OH, —O—C$_1$–C$_6$-alkyl, —S—C$_1$–C$_6$-alkyl, —NR$^6$R$^7$, an aryl group optionally mono or polysubstituted by halogen atoms, —NO$_2$, —SO$_2$H, or C$_1$–C$_4$-alkyl; and n and m, which are identical or different, are each 0, 1, 2, or 3, with the proviso that naphtho[1,8-de]-2,3-dihydro-1,1-dioxide-1,2-thiazine is excluded, or an enantiomer or diastereomer thereof, or a pharmacologically acceptable salt thereof.

2. The compound of formula (I) according to claim 1, wherein:

R$^1$ is selected from hydrogen, a C$_1$–C$_6$-alkyl group optionally substituted by one or more halogen atoms, —SO$_2$H, —SO$_2$—C$_1$–C$_6$-alkyl, —SO—C$_1$–C$_6$-alkyl, —CO—$C_1$–$C_6$-alkyl, —$C_1$–$C_4$-alkyl-$NR^7R^8$, —$C_1$–$C_4$-alkyl-O—$C_1$–$C_4$-alkyl, or benzyl, $R^2$ and $R^3$, which are identical or different, are each selected from hydrogen, a $C_1$–$C_6$-alkyl group optionally substituted by one or more halogen atoms, halogen, —$NO_2$, —$SO_2H$, —$SO_2$—$C_1$–$C_6$-alkyl, —SO—$C_1$–$C_6$-alkyl, —CO—$C_1$–$C_6$-alkyl, —OH, —O—$C_1$–$C_6$-alkyl, —S—$C_1$–$C_6$-alkyl, —$C_1$–$C_4$-alkyl-$NR^7R^8$, or —$C_1$–$C_4$-alkyl-O—$C_1$–$C_4$-alkyl, or $R^1$ and $R^2$ together are a $C_4$–$C_6$-alkylene bridge;

$R^6$ and $R^7$, which are identical or different, are each hydrogen, $C_1$–$C_4$-alkyl, or —CO—$C_1$–$C_2$-alkyl, and $R^4$, which are identical or different, are each selected from a $C_1$–$C_6$-alkyl group optionally substituted by one or more halogen atoms, halogen, —CN, —$NO_2$, —$SO_2H$, —$SO_3H$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—$NR^6R^7$, —OH, —O—$C_1$–$C_6$-alkyl, —S—$C_1$–$C_6$-alkyl, or —$NR^6R^7$;

$R^5$, which are identical or different, are each selected from a $C_1$–$C_6$-alkyl group optionally substituted by one or more halogen atoms, halogen, —CN, —$NO_2$, —$SO_2H$, —$SO_3H$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—$NR^6R^7$, —OH, —O—$C_1$–$C_6$-alkyl, —S—$C_1$–$C_6$-alkyl, and —$NR^6R^7$; or n and m, which are identical or different, are each 0, 1, or 2, or an enantiomer or diastereomer thereof, or a pharmacologically acceptable salt thereof.

3. The compound of formula (I) according to claim 1, wherein:

$R^1$ is hydrogen, $C_1$–$C_4$-alkyl, or benzyl, $R^2$ and $R^3$, which are identical or different, are each hydrogen or $C_1$–$C_4$-alkyl, or $R^1$ and $R^2$ together are a butylene bridge;

$R^4$, which are identical or different, are each selected from a $C_1$–$C_6$-alkyl group optionally substituted by one or more halogen atoms, halogen, —CN, —$NO_2$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—$NR^6R^7$, —OH, —O—$C_1$–$C_6$-alkyl, —S—$C_1$–$C_6$-alkyl, or —$NR^6R^7$;

$R^5$, which are identical or different, are each selected from a $C_1$–$C_6$-alkyl group optionally substituted by one or more halogen atoms, halogen, —CN, —$NO_2$, —COOH, —CO—$C_1$–$C_6$-alkyl, —O—CO—$C_1$–$C_4$-alkyl, —CO—O—$C_1$–$C_4$-alkyl, —O—CO—O—$C_1$–$C_4$-alkyl, —CO—$NR^6R^7$, —OH, —O—$C_1$–$C_6$-alkyl, —S—$C_1$–$C_6$-alkyl, or —$NR^6R^7$; and n and m, which are identical or different, are each 0, 1, or 2, or an enantiomer or diastereomer thereof, or a pharmacologically acceptable salt thereof.

4. The compound of formula (I) according to claim 1, wherein:

$R^1$, $R^2$, $R^3$, which are identical or different, are each hydrogen or $C_1$–$C_4$-alkyl;

$R^4$, which are identical or different, are each selected from a $C_1$–$C_6$-alkyl group optionally substituted by one or more halogen atoms, halogen, —$NO_2$, —O—CO—$C_1$–$C_4$-alkyl, —O—CO—O—$C_1$–$C_4$-alkyl, —O—$C_1$–$C_6$-alkyl, or —$NR^6R^7$;

$R^5$, which are identical or different, are each selected from a $C_1$–$C_6$-alkyl group optionally substituted by one or more halogen atoms, halogen, —$NO_2$, —O—CO—$C_1$–$C_4$-alkyl, —O—CO—O—$C_1$–$C_4$-alkyl, —O—$C_1$–$C_6$-alkyl, or —$NR^6R^7$; and n and m, which are identical or different, are each 0, 1, or 2, or an enantiomer or diastereomer thereof, or a pharmacologically acceptable salt thereof.

5. The compound of formula (I) according to claim 1, wherein:

$R^1$ is methyl, ethyl, isopropyl, n-butyl, or benzyl, or an enantiomer or diastereomer thereof, or a pharmacologically acceptable salt thereof.

6. The compound of formula (I) according to claim 1, wherein:

$R^1$ is methyl, or a pharmacologically acceptable salt thereof.

7. The compound of formula (I) according to claim 1, wherein:

$R^1$ is methyl;

$R^2$ and $R^3$ are each hydrogen;

$R^4$ and $R^5$, which are identical or different, are each halogen; and n and m, which are identical or different, are each 0, 1, or 2, or a pharmacologically acceptable salt thereof.

* * * * *